(12) United States Patent
Chang et al.

(10) Patent No.: US 10,466,089 B1
(45) Date of Patent: Nov. 5, 2019

(54) TESTING MODULE AND MEASURING APPARATUS HAVING THE SAME

(71) Applicant: CORETECH SYSTEM CO., LTD., Chupei, Hsinchu County (TW)

(72) Inventors: Yuing Chang, Chupei (TW); Rong-Yeu Chang, Chupei (TW); De-Lung Lai, Chupei (TW); Chia-Hsiang Hsu, Chupei (TW)

(73) Assignee: CORETECH SYSTEM CO., LTD., Chupei, Hsinchu County (TW)

( * ) Notice: Subject to any disclaimer, the term of this patent is extended or adjusted under 35 U.S.C. 154(b) by 0 days.

(21) Appl. No.: 16/145,960

(22) Filed: Sep. 28, 2018

(51) Int. Cl.
| | | |
|---|---|---|
| G01F 22/02 | (2006.01) | |
| G01N 9/02 | (2006.01) | |
| G01N 33/44 | (2006.01) | |

(52) U.S. Cl.
CPC ............... *G01F 22/02* (2013.01); *G01N 9/02* (2013.01); *G01N 33/442* (2013.01)

(58) Field of Classification Search
CPC ....................................................... G01F 22/02
See application file for complete search history.

(56) References Cited

U.S. PATENT DOCUMENTS

| | | | | | |
|---|---|---|---|---|---|
| 1,806,037 | A | * | 5/1931 | Black | C10G 11/08 |
| | | | | | 196/106 |
| 4,171,341 | A | * | 10/1979 | Morgan | G01N 27/626 |
| | | | | | 422/98 |
| 4,342,518 | A | * | 8/1982 | Shirley | G01N 33/24 |
| | | | | | 374/51 |
| 6,171,286 | B1 | * | 1/2001 | Gross | A61M 5/315 |
| | | | | | 604/218 |
| 6,221,203 | B1 | * | 4/2001 | Lin | H01L 21/67103 |
| | | | | | 118/723 R |
| 2002/0189536 | A1 | * | 12/2002 | Otsuki | C30B 29/36 |
| | | | | | 117/109 |
| 2008/0073517 | A1 | * | 3/2008 | Melville | G02B 7/008 |
| | | | | | 250/306 |
| 2010/0286932 | A1 | * | 11/2010 | Caldwell | G01F 22/02 |
| | | | | | 702/55 |
| 2013/0243028 | A1 | * | 9/2013 | Singh | G01N 33/2823 |
| | | | | | 374/43 |

* cited by examiner

*Primary Examiner* — Lisa M Caputo
*Assistant Examiner* — Alex T Devito
(74) *Attorney, Agent, or Firm* — Muncy, Geissler, Olds & Lowe, P.C.

(57) ABSTRACT

The present disclosure provides a measuring apparatus including a testing module. The testing module includes: a temperature-controlling cylinder having a top opening and a bottom opening; an upper piston and a lower piston respectively seal the top opening and the bottom opening of the temperature-controlling cylinder so that a testing chamber is formed inside the temperature-controlling cylinder, wherein the testing chamber has a longitudinal length; and a pipe surrounding the testing chamber along the longitudinal length in such a way that when a wire is provided along and in the pipe with a number of turns, a density of the turns has at least two different values over the longitudinal length.

20 Claims, 17 Drawing Sheets

600

102

604

606

108

TESTING MODULE AND MEASURING APPARATUS HAVING THE SAME

TECHNICAL FIELD

The present disclosure relates to measuring equipment, and more particularly, to a measuring apparatus designed for measuring a volumetric variation of a resin under different temperatures and pressures.

DISCUSSION OF THE BACKGROUND

During an injection molding operation performed using a plastic material, shrinkage rate and warpage rate are critical variables, which can be predicted from the relationship among pressure (P), specific volume (V), and temperature (T) (known as the PVT properties) of the plastic material.

Normally, when measuring the PVT properties of the plastic material, the volumetric variation of the plastic material is measured under isobaric or isothermal conditions provided by a measuring apparatus.

During a conventional measuring process, the plastic material may lack uniformity of density due to non-uniform temperature distribution, and volumetric measurement errors may occur as a result. In addition, the plastic material may leak, or elements of the measuring apparatus may stick or rub against each other due to non-uniform temperature distribution.

This Discussion of the Background section is for background information only. The statements in this Discussion of the Background are not an admission that the subject matter disclosed in this section constitutes a prior art to the present disclosure, and no part of this section may be used as an admission that any part of this application, including this Discussion of the Background section, constitutes prior art to the present disclosure.

SUMMARY

The present disclosure provides a measuring apparatus for measuring a volumetric variation of a resin under different temperatures and pressures. In some embodiment, the measuring apparatus comprises a testing module. In some embodiments, the testing module comprises: a temperature-controlling cylinder having a top opening and a bottom opening; an upper piston and a lower piston respectively sealing the top opening and the bottom opening of the temperature-controlling cylinder so that a testing chamber is formed inside the temperature-controlling cylinder, wherein the testing chamber has a longitudinal length; and a pipe surrounding the testing chamber along the longitudinal length in such a way that when a wire is provided along and in the pipe in a spiral formation with a number of turns, a density of the turns has at least two different values over the longitudinal length of the testing chamber.

In some embodiments, the pipe is constructed by a sleeve and an external wall of the temperature-controlling cylinder sealed against each other.

In some embodiments, the density of the turns increases toward the top opening and the bottom opening of the temperature-controlling cylinder.

In some embodiments, when a wire is provided along and in the pipe and a liquid flows in the pipe, the wire is isolated from the liquid by a component formed by brazing.

In some embodiments, the upper piston has a wire and a pipe that are positioned at different surface levels in such a way that the wire is closer than the pipe to the testing chamber.

In some embodiments, the upper piston has a connecting element attached to the measuring apparatus by means of a ball joint.

In some embodiments, a size of the lower piston is designed so that a pressure in the testing chamber changes with movement of the lower piston relative to the testing chamber along the longitudinal length.

In some embodiments, the lower piston comprises a body having a hole configured for receiving a heating device, a fluid inlet at first end of the hole, a fluid outlet at second end of the hole, and a groove on an outer surface of the body, wherein the groove extends from the second end to the first end.

In some embodiments, an annular pipe is formed in the temperature-controlling cylinder and surrounds the lower piston.

In some embodiments, a plurality of temperature transducers are inserted into the temperature-controlling cylinder from several positions on the temperature-controlling cylinder that do not overlap the pipe and are arranged to detect a temperature distribution in the testing chamber.

The present disclosure also provides a measuring apparatus for measuring a volumetric variation of a resin under different temperatures and pressures. In some embodiment, the measuring apparatus comprises a testing module. In some embodiments, the testing module comprises: a temperature-controlling cylinder having a first internal surface and a first external surface; a testing tube having a second external surface, received in the temperature-controlling cylinder with the second external surface facing the first internal surface; and an upper piston and a lower piston respectively sealing a top opening and a bottom opening of the testing tube so that a testing chamber is formed inside the testing tube, wherein the testing chamber has a longitudinal length; wherein a wire is provided on the first external surface, surrounding the testing chamber with a number of turns; and wherein a pipe is formed between the second external surface and the first internal surface, surrounding the testing chamber along the longitudinal length.

In some embodiments, a groove is formed on the first external surface for providing the wire.

In some embodiments, a density of the turns increases toward the top opening and the bottom opening of the testing tube.

In some embodiments, a spiral groove is formed on the second external surface and the pipe is formed by the second external surface and the first internal surface sealing against each other.

In some embodiments, a spiral groove is formed on the first internal surface and the pipe is formed by the second external surface and the first internal surface sealing against each other.

In some embodiments, the upper piston has a wire and a cooling pipe that are positioned at different surface levels in such a way that the wire is closer than the cooling pipe to the testing chamber.

In some embodiments, the upper piston has a connecting element attached to the measuring apparatus by means of a ball joint.

In some embodiments, a size of the lower piston is designed so that a pressure in the testing chamber changes with movement of the lower piston relative to the testing chamber along the longitudinal length.

In some embodiments, the lower piston comprises a body having a hole configured for receiving a heating device, a fluid inlet at first end of the hole, a fluid outlet at second end of the hole, and a groove on an outer surface of the body, wherein the groove extends from the second end to the first end.

In some embodiments, a plurality of temperature transducers are inserted into the testing tube from several positions not covered by the pipe and are arranged to detect a temperature distribution in the testing chamber.

The foregoing has outlined rather broadly the features and technical advantages of the present disclosure in order that the detailed description of the disclosure that follows may be better understood. Additional features and technical advantages of the disclosure are described hereinafter, and form the subject of the claims of the disclosure. It should be appreciated by those skilled in the art that the concepts and specific embodiments disclosed may be utilized as a basis for modifying or designing other structures, or processes, for carrying out the purposes of the present disclosure. It should also be realized by those skilled in the art that such equivalent constructions do not depart from the spirit or scope of the disclosure as set forth in the appended claims.

BRIEF DESCRIPTION OF THE DRAWINGS

A more complete understanding of the present disclosure may be derived by referring to the detailed description and claims. The disclosure should also be understood to be connected to the figures' reference numbers, which refer to similar elements throughout the description.

DETAILED DESCRIPTION

Figure 1A:
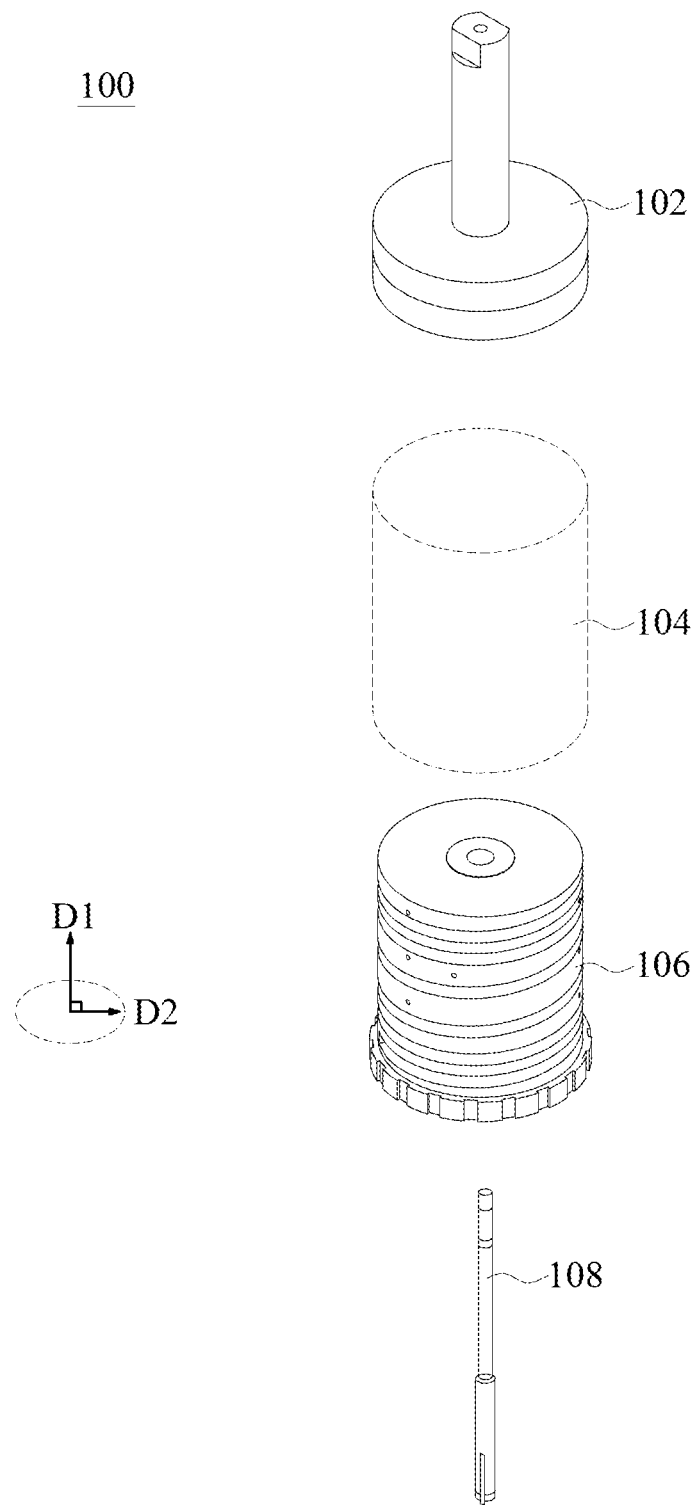
FIG. 1A is an exploded perspective vie of a testing module in accordance with some embodiments of the present disclosure.

Embodiments, or examples, of the disclosure illustrated in the drawings are now described using specific language. It shall be understood that no limitation of the scope of the disclosure is hereby intended. Any alteration or modification of the described embodiments, and any further applications of principles described in this document, are to be considered as normally occurring to one of ordinary skill in the art to which the disclosure relates. Reference numerals may be repeated throughout the embodiments, but this does not necessarily mean that feature(s) of one embodiment apply to another embodiment, even if they share the same reference numeral.

It shall be understood that, although the terms first, second, third, etc. may be used herein to describe various elements, components, regions, layers or sections, these elements, components, regions, layers or sections are not limited by these terms. Rather, these terms are merely used to distinguish one element, component, region, layer or section from another region, layer or section. Thus, a first element, component, region, layer or section discussed below could be termed a second element, component, region, layer or section without departing from the teachings of the present inventive concept.

The terminology used herein is for the purpose of describing particular example embodiments only and is not intended to be limited to the present inventive concept. As used herein, the singular forms "a," "an" and "the" are intended to include the plural forms as well, unless the context clearly indicates otherwise. It shall be further understood that the terms "comprises" and "comprising," when used in this specification, point out the presence of stated features, integers, steps, operations, elements, or components, but do not preclude the presence or addition of one or more other features, integers, steps, operations, elements, components, or groups thereof.

Figure 1B:
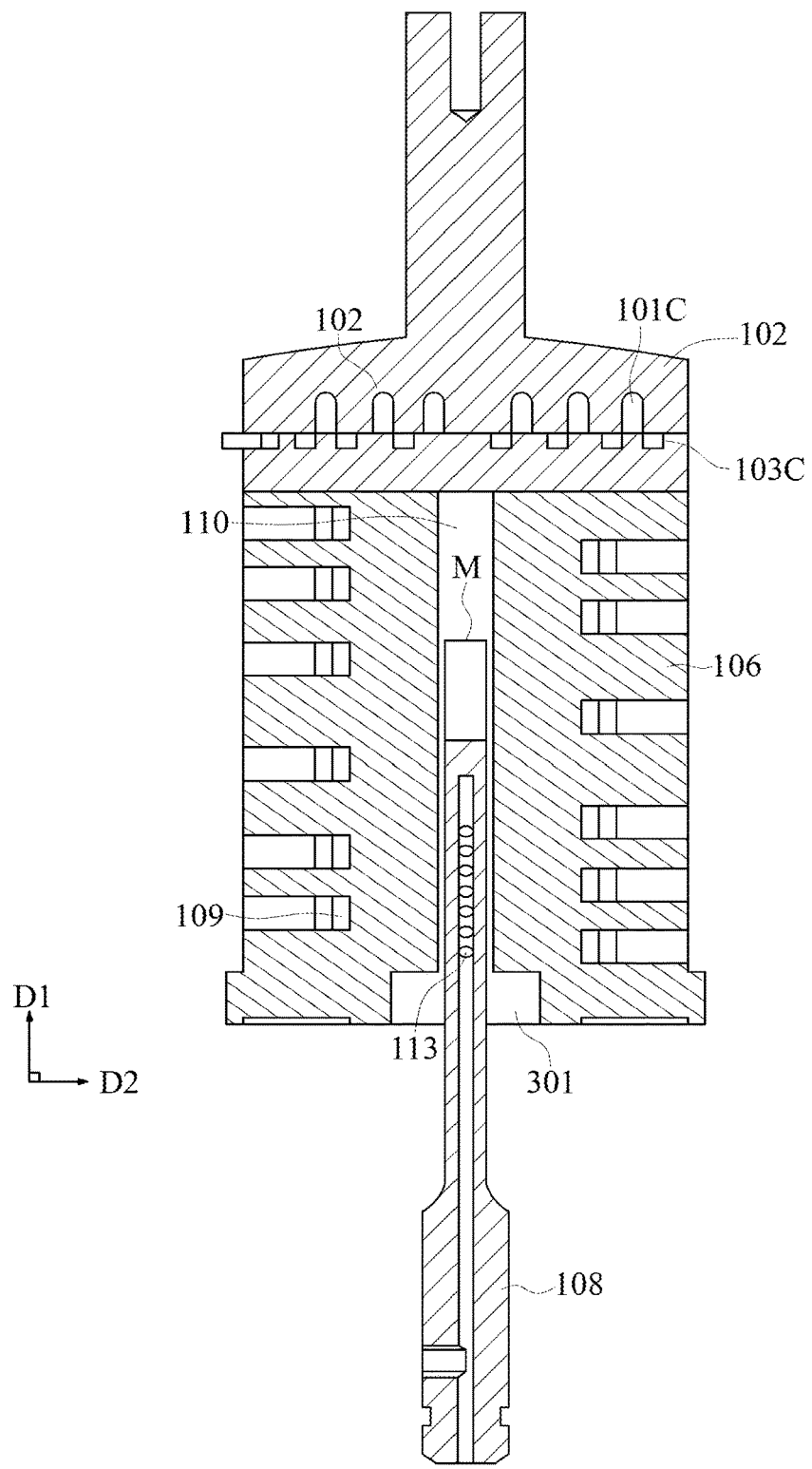
FIG. 1B is a cross-sectional view of an upper piston, a lower piston and a temperature-controlling cylinder of the testing module in accordance with some embodiments of the present disclosure.

FIG. 1A is an exploded perspective view of a testing module 100 in accordance with some embodiments of the present disclosure. FIG. 1B is a cross-sectional view of an upper piston, a lower piston and a temperature-controlling cylinder of the testing module 100 in accordance with some embodiments of the present disclosure.

Referring to FIG. 1A, in some embodiments, the testing module 100 comprises a temperature-controlling cylinder 106, an upper piston 102, and a lower piston 108. In some embodiments, the testing module 100 further comprises a sleeve 104. The temperature-controlling cylinder 106, the upper piston 102, and the lower piston 108 can be assembled together generally along an axial direction D1. For example, the relative movements of their geometric centers are along the axial direction D1 in an assembly or disassembly process. A radial direction D2 is defined as any direction perpendicular to the axial direction D1.

Figure 9A:
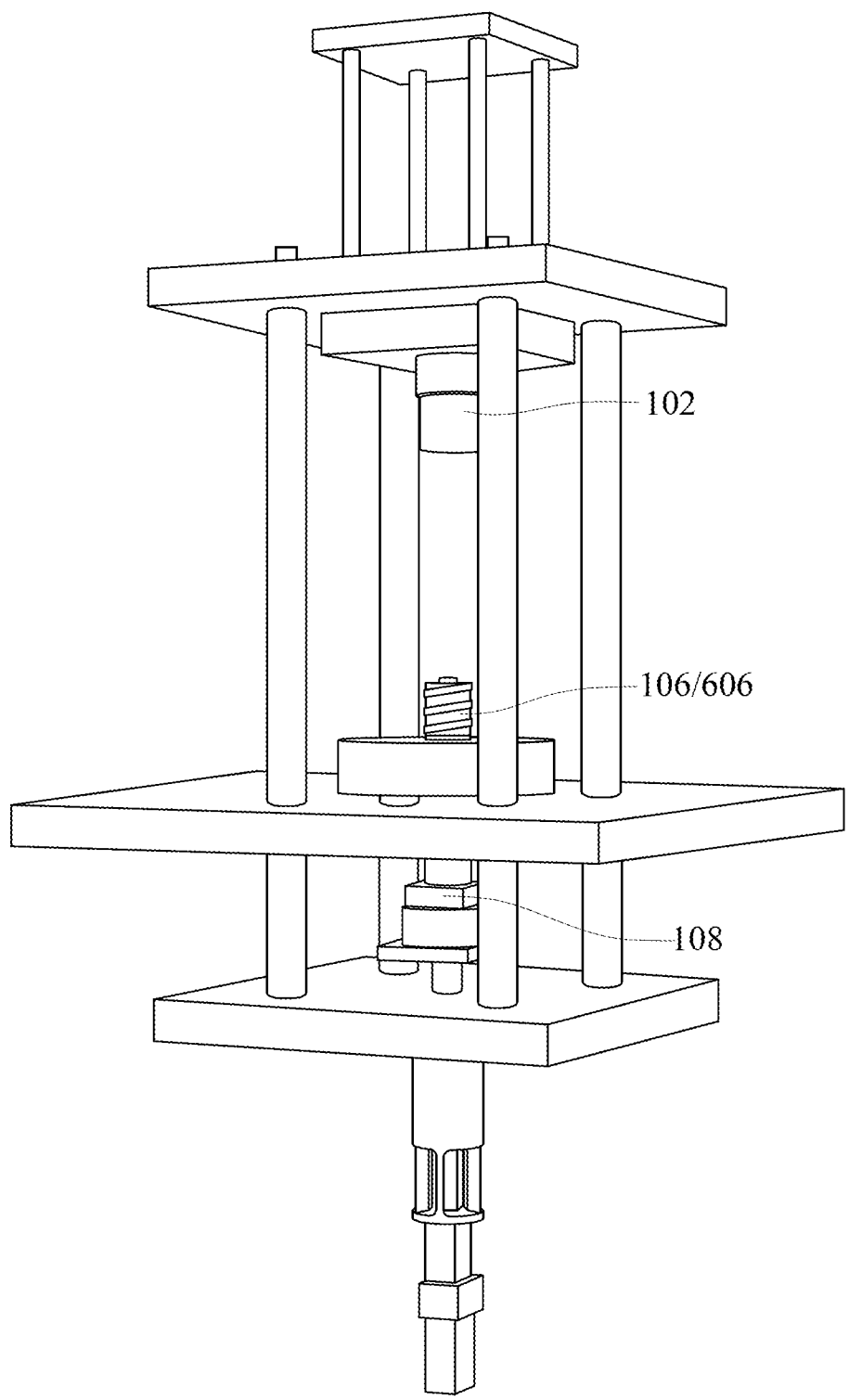
FIG. 9A is a perspective view of a measuring apparatus with the testing module in accordance with some embodiments of the present disclosure.
Figure 9B:
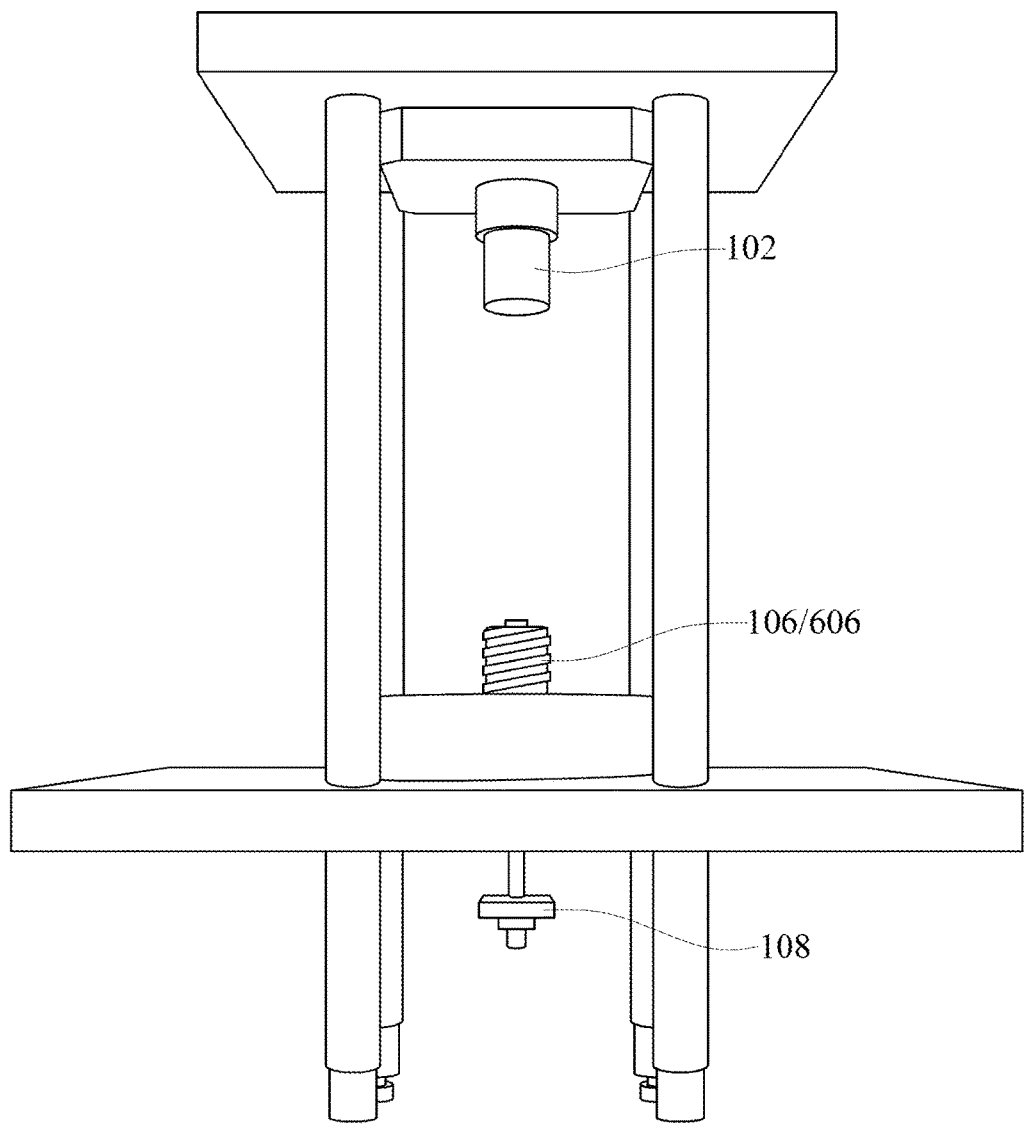
FIG. 9B is a front view of the measuring apparatus in FIG. 9A in accordance with some embodiments of the present disclosure.

It should be noted that the testing module 100 is installed in a measuring apparatus when used, such installation is shown in FIGS. 9A and 9B. The measuring apparatus holds and calibrates the testing module 100. The measuring apparatus also connects to a cooling fluid tank and a fluid exhaust container. In some embodiments, the cooling fluid tank provides cooling fluid to cool the measuring apparatus and the testing module 100 inside. In some embodiments, the cooling fluid is vortex tube cooling gas for achieving rapid cooling. The flow passages of the cooling fluid in the testing module 100 will be discussed in detail below.

Referring to FIG. 1B, in some embodiments, during a measuring process, a top opening of the temperature-controlling cylinder 106 is sealed by the upper piston 102, and a bottom opening of the temperature-controlling cylinder 106 is sealed by the lower piston 108. In some embodiments, a testing chamber 110 is formed in the temperature-controlling cylinder 106, wherein the testing chamber 110 has a longitudinal length L (not shown in the figures) in the axial direction D1. In some embodiments, the longitudinal length L is measured from the top to the bottom of the testing chamber 110, wherein the longitudinal length L is the length of a space which is able to contain a specimen M in the testing chamber 110. In some embodiments, the specimen M comprises a resin, such as a molding material. In some embodiments, the molding material comprises the thermoplastic resin or the thermosetting resin.

In some embodiments, the testing chamber 110 is configured to contain the specimen M and keep the specimen M in a specific environment, for examples, an isobaric environment or an isothermal environment during a measurement process. It is expected that a temperature distribution in the testing chamber 110 is uniform, so as to provide homogeneous heating to the specimen M under either an isobaric environment or an isothermal environment. After a measurement process, it is expected that the testing module 100 can be cooled quickly, so as to reduce the cooling time.

In some embodiments, the testing chamber 110 is designed and shaped to receive the lower piston 108, and a portion of the lower piston 108 slides in the temperature-controlling cylinder 106. The specimen M is placed on an end of the lower piston 108 in the testing chamber 110.

In some embodiments, relative sizes of the lower piston 108 and the testing chamber 110 are designed so that a pressure in the testing chamber 110 changes with movement of the lower piston 108 relative to the testing chamber 110 along the longitudinal length L.

Figure 2A:
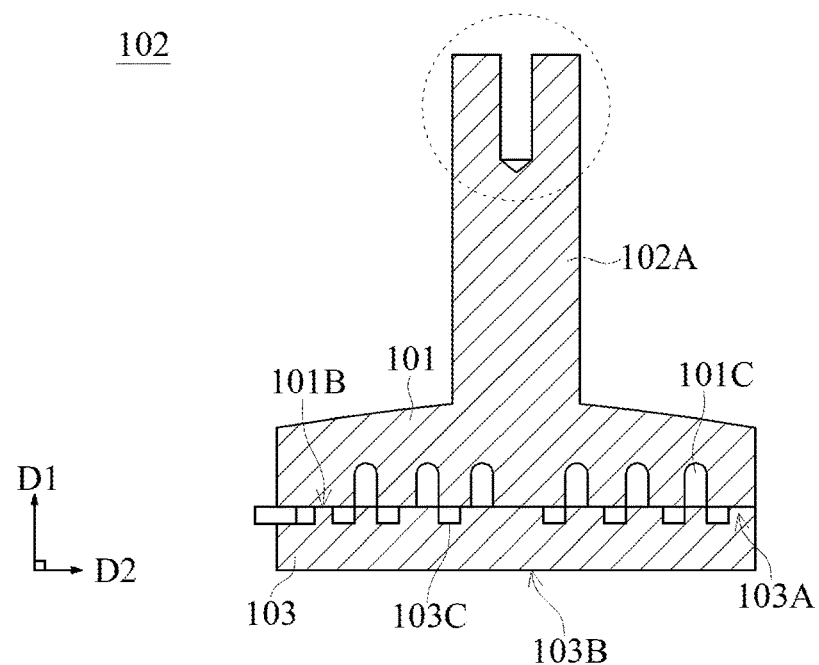
FIG. 2A is a cross-sectional view of an upper piston of the testing module in accordance with some embodiments of the present disclosure.
Figure 2B:
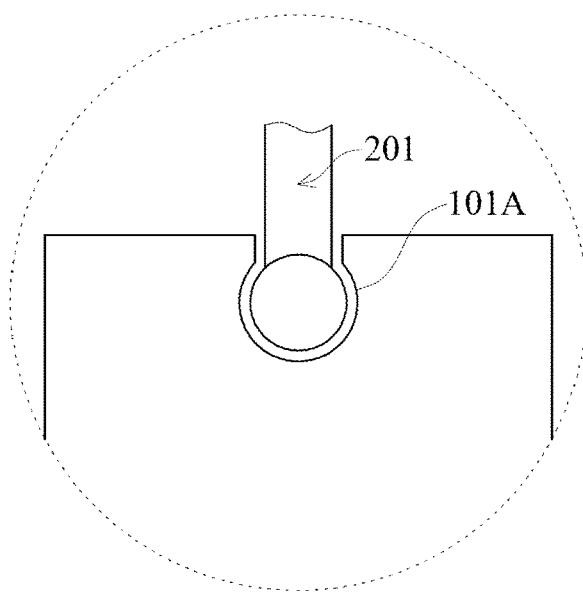
FIG. 2B is a partial enlarged view of an upper piston of the testing module in accordance with some embodiments of the present disclosure.
Figure 2C:
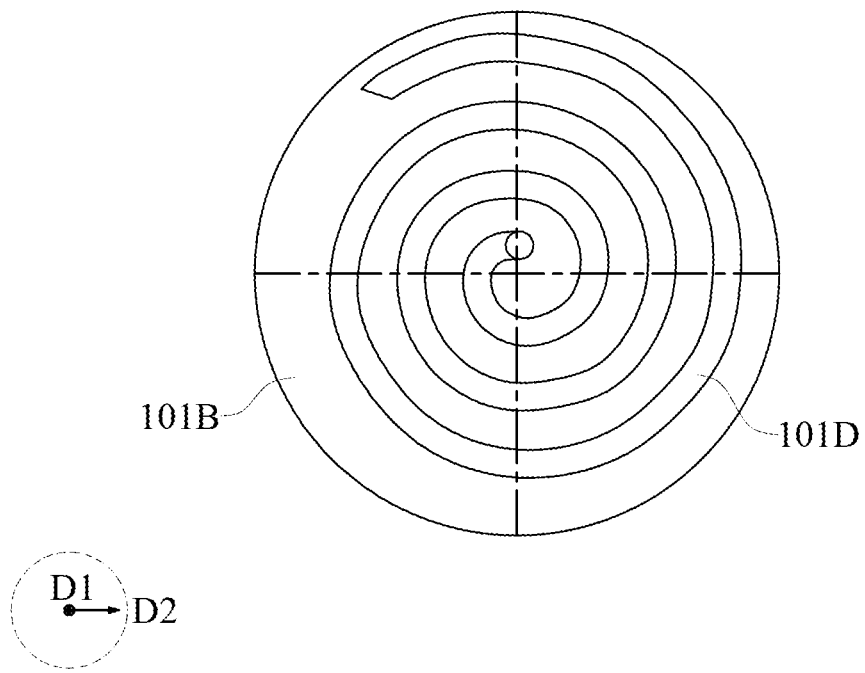
FIG. 2C is a top view of an upper piston of the testing module in accordance with some embodiments of the present disclosure.
Figure 2C:
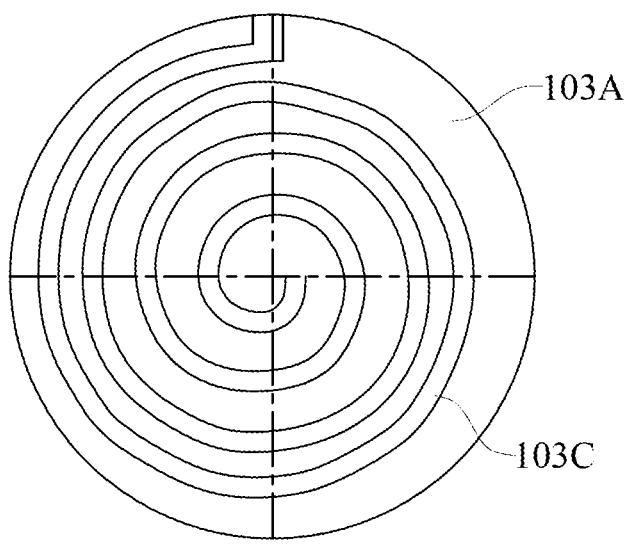

FIGS. 2A to 2C illustrate a cross-sectional view, a close-up view, and top views of the upper piston 102 of the testing module 100 in accordance with some embodiments of the present disclosure.

Referring to FIG. 2A, in some embodiments, the upper piston 102 has a first disk part 101 and a second disk part 103, wherein a surface 103A of the second disk part 103 attached to a surface 101B of the first disk part 101 by welding. In some embodiments, the second disk part 103 seals with the top opening of the temperature-controlling cylinder 106 by a surface 103B opposite to the surface 103A.

Still referring to FIG. 2A, in some embodiments, the first disk part 101 has a receiving hole 101A on a surface opposite to the surface 101B. In some embodiments, the receiving hole 101A is at an end of a stick 102A, projecting from the surface opposite to the surface 101B. In some embodiments, the stick 102A projects from a center point of the surface opposite to the surface 101B.

Referring to FIG. 2B, the receiving hole 101A is configured to attach the first disk part 101 to the measuring apparatus by means of a ball joint, for example, receiving a stick 201 of the measuring apparatus in the receiving hole 101A. In some embodiments, the receiving hole 101A and the stick 201 are rotatable with respect to each other after they are attached. For example, the stick 201 has a spherical end and the receiving hole 101A is a spherical hole for containing the spherical end and allowing the spherical end to rotate and move within the spherical hole. The contours of the receiving hole 101A and the end of the stick 201 may be similar from a cross-sectional view, but the disclosure is not limited thereto.

Referring back to FIG. 2A, in some embodiments, the upper piston 102 has a wire 103C and a pipe 101C that are positioned at different surface levels along the axial direction D1, wherein the surface levels have a normal direction parallel to the axial direction D1. For example, when the surface 103B is sealed against the temperature-controlling cylinder 106, the wire 103C is closer to the temperature-controlling cylinder 106 than to the pipe 101C. In some embodiments, the wire 103C is in the second disk part 103. In some embodiments, the pipe 101C is in the first disk part 101.

Referring to FIG. 2C, in some embodiments, a groove 101D is recessed into the surface 101B of the first disk part 101 along the first direction D1. In some embodiments, the groove 101D has a spiral structure as viewed from above in FIG. 2C and appears jagged in the cross-sectional view of FIG. 2A.

In some embodiments, when the surface 103A of the second disk part 103 is attached to the first disk part 101, the groove 101D is sealed by the surface 103A and thus forms a pipe structure, i.e. the pipe 101C. In some embodiments, the pipe structure has one end connected to the cooling fluid tank and another end connected to the fluid exhaust container. As mentioned above, the cooling fluid can be vortex tube cooling gas for achieving rapid cooling.

Still referring to FIG. 2C, in some embodiments, a wire 103C is implanted in the second disk part 103. In some embodiments, the surface level of the wire 103C in the second disk part 103 may be designed to, for example, be adjacent to the surface 103A, be on the surface 103A without being covered, or be closer to the surface 103B. In some embodiments, the wire 103C is disposed in a spiral pattern starting from the center point D1 as seen from the top view in FIG. 2C. In some embodiments, the wire 103C is configured to heat the testing module 100, and has one end connected to a power supply.

In some embodiments, the wire 103C and the pipe 101C are arranged in a staggered manner in relation to each other as shown in the cross-sectional view of FIG. 2A, and do not overlap when viewed from the top view. In some embodiments, the density of the spiral structure of the pipe 101C is greater than the density of the wire 103C. For example, the total length of the pipe 101C in first disk part 101 is greater than the total length of the wire 103B in the second disk part 103 as shown in FIG. 2C.

In some embodiments, the wire 103C and the pipe 101C in the upper piston 102 can help control the temperature in the testing module 100, and can help maintain a uniform temperature distribution during a measurement process and achieve rapid cooling after the measurement process.

Figure 3A:
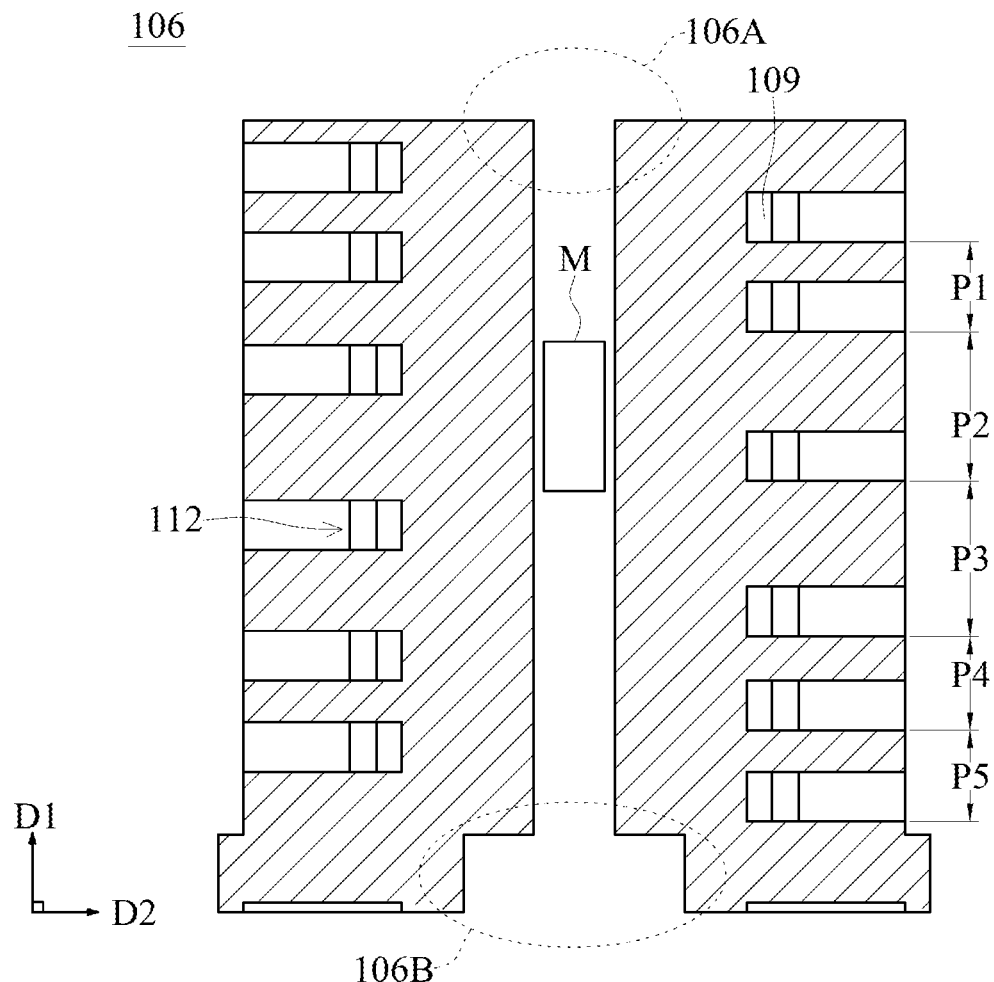
FIG. 3A is a cross-sectional view of a temperature-controlling cylinder of the testing module in accordance with some embodiments of the present disclosure.
Figure 3B:
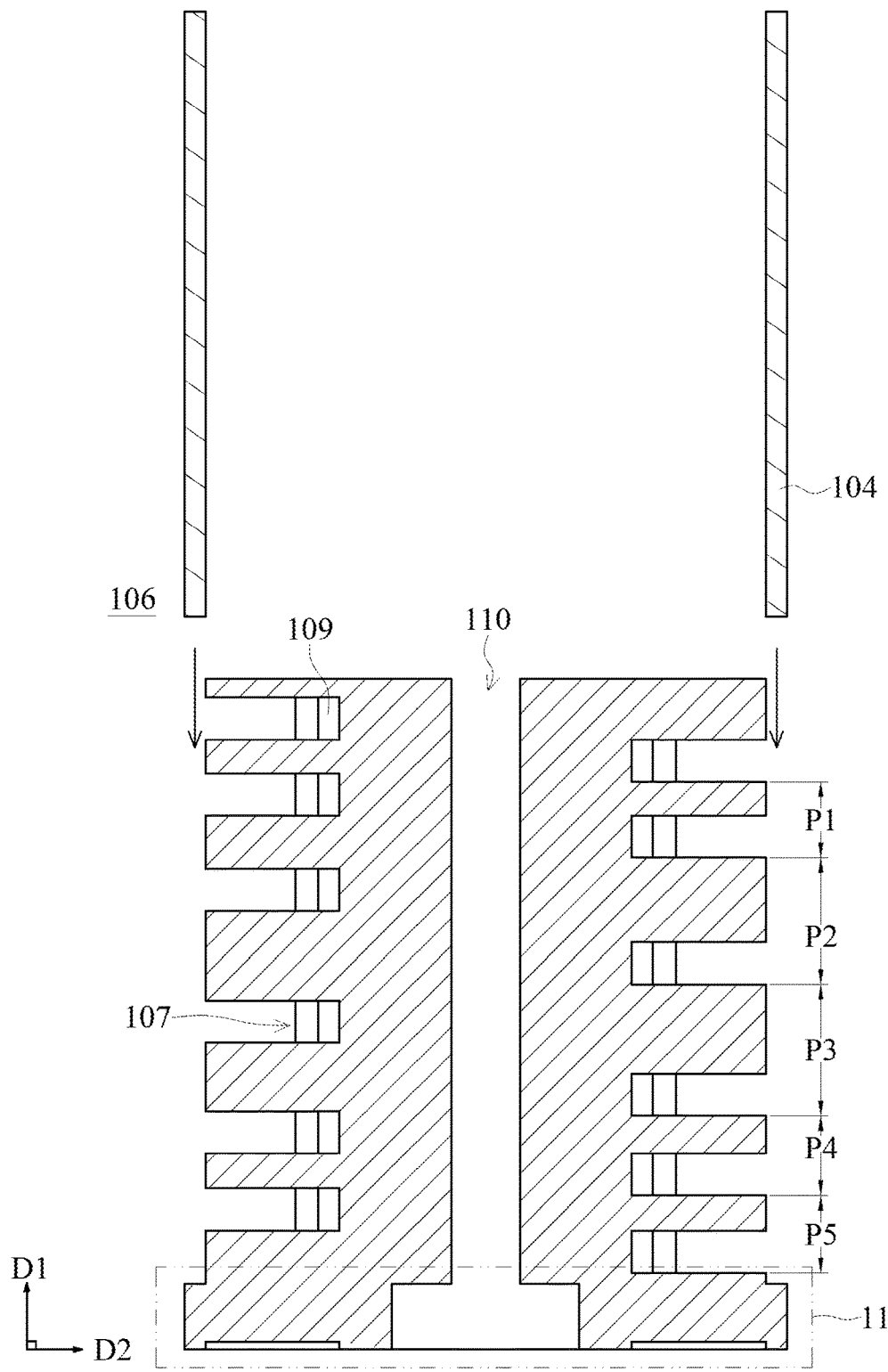
FIG. 3B is a cross-sectional view of a temperature-controlling cylinder and a sleeve of the testing module in accordance with some embodiments of the present disclosure.
Figure 3C:
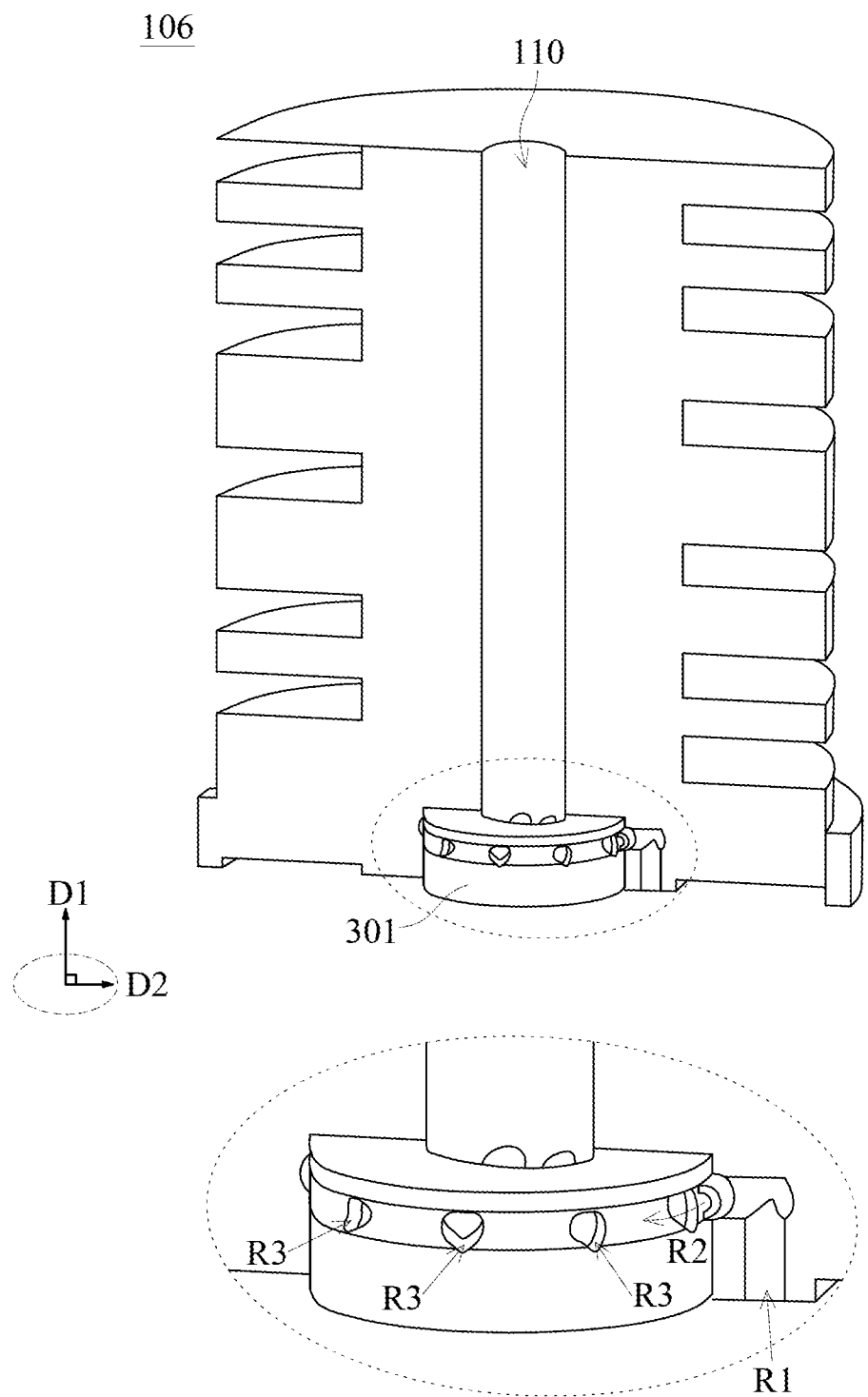
FIG. 3C is a cross-sectional view of a temperature-controlling cylinder of the testing module, wherein an annular cooling channel is shown in a perspective view in accordance with some embodiments of the present disclosure.

FIGS. 3A to 3C are cross-sectional views of the temperature-controlling cylinder 106 of the testing module 100 in accordance with some embodiments of the present disclosure, with FIG. 3B further illustrating the sleeve 104 and FIG. 3C further illustrating an annular cooling channel in a perspective view.

Referring to FIG. 3A, in some embodiments, the temperature-controlling cylinder 106 extends in the axial direction D1. In some embodiments, the temperature-controlling cylinder 106 has the top opening 106A and the bottom opening 106B that are respectively sealed by the upper piston 102 and the lower piston 108 during a measuring process.

Still referring to FIG. 3A, in some embodiments, a pipe 112 surrounds the temperature-controlling cylinder 106 and winds in a spiral manner along the axial direction D1. In some embodiments, when the openings of the temperature-controlling cylinder 106 are sealed, the pipe 112 also surrounds a testing chamber 110 and extends in a spiral manner along the longitudinal length L.

In some embodiments, the pipe 112 has one end connected to the cooling fluid tank and another end connected to the fluid exhaust container. As mentioned above, in some embodiments, the cooling fluid can be vortex tube cooling gas for achieving rapid cooling. With the vortex tube cooling gas flowing in the pipe 112, the heat of the testing module 100 can be removed quickly after a measuring process.

In some embodiments, a wire 109 is provided along and in the pipe 112 with a number of turns, and a density of the turns has at least two different values over the longitudinal length L. For example, as shown in the cross-sectional view of FIG. 3A, a pitch of the spiral of the pipe 112 is calculated based on a diameter of the pipe 112 and a spacing between parallel sections of the pipe 112. In some embodiments, a pitch measured closer to the openings of the temperature-controlling cylinder 106 is less than a pitch measured farther from the openings.

As shown in FIG. 3A, in some embodiments, the pitch P1 and the pitch P5 are less than the pitch P3. In some embodiments in which the wire 109 is provided, the pitch of the pipe 112 also defines the density of the turns of the wire 109. For example, the density of the turns is measured by dividing an amount of turns within a length in the axial direction D1 by the length in the axial direction D1; thus, given a fixed length, a greater amount of turns correlates with a greater density of the turns.

In some embodiments, when the pitch closer to the openings of the temperature-controlling cylinder 106 is less than the pitch farther from the openings, the amount of turns closer to the openings of the temperature-controlling cylinder 106 is greater and the density of the turns closer to the openings of the temperature-controlling cylinder 106 is accordingly greater. In some embodiments, the density of the turns increases closer the top opening 106A and the bottom opening 106B of the temperature-controlling cylinder 106.

Still referring to FIG. 3A, in some embodiments, the wire 109 is configured to heat the testing module 100, and has one end connected to a power supply. In some embodiments, during a measuring process, a temperature distribution in the testing chamber 110 may be not uniform due to the accumulation of internal heat, that is, the temperature in the middle of the testing chamber 110 is greater than the temperature on the ends of the testing chamber. If the density of the wire turns is greater on the ends than in the middle, then the heat that provided to the ends of the testing chamber 110 can be less than the heat provided to the middle of the testing chamber 110. Therefore, the internal heat accumulation can be avoided and the temperature distribution in the testing chamber 110 during a measurement process can be more uniform.

In some embodiments, the pipe 112 has one end connected to the cooling fluid tank and another end connected to the fluid exhaust container, while the wire 109 has one end connected to the power supply. In some embodiments, the wire 109 is isolated from the fluid flowing in the pipe 112 by means of a component formed by, for example, brazing. In some embodiments, to avoid empty burning, the wire 109 is brazed in such a way as to be isolated from the fluid and the surrounding environment.

In some embodiments, the testing module 100 further comprises the sleeve 104. In some embodiments, the pipe 112 is formed by the sleeve 104 and an external wall of the temperature-controlling cylinder 106 sealed against each other. Referring to FIG. 3B, in some embodiment, a groove 107 is recessed in an external surface of the temperature-controlling cylinder 106 approximately parallel to the radial direction D2. In some embodiments, the groove 107 surrounds the testing chamber 110 and winds in a spiral manner along the axial direction D1.

In some embodiments, the groove 107 has a varying pitch. For example, as shown in the cross-sectional view of FIG. 3B, the groove 107 has recessed portions and protruding portions staggered alternatingly. In some embodiments, a pitch of the groove 107 is defined as the width of one recessed portion plus the width of one protruding portion along the axial direction D1. In some embodiments, a pitch closer to the openings of the temperature-controlling cylinder 106 is shorter. As shown in FIG. 3B, in some embodiments, the pitch P1 and the pitch P5 are smaller than the pitch P3. In some embodiments, the groove 107 has a varying pitch that decreases toward the openings of the temperature-controlling cylinder 106 over the longitudinal length L.

In some embodiments, the wire 109 is brazed at the deepest surfaces in the recessed portions of the groove 107.

Still referring to FIG. 3B, in some embodiments, the sleeve 104 surrounds the temperature-controlling cylinder 106. In some embodiments, the sleeve 104 extends in the axial direction D1. In some embodiments, the sleeve 104 is installed around the external surface of the temperature-controlling cylinder 106 with, for example, one end welded at a bottom base 111 of the temperature-controlling cylinder 106. In some embodiments, the bottom base 111 projects in the radial direction D2 from the external surface of the temperature-controlling cylinder 106. In some embodiments, the bottom base 111 can be deemed as the most protruding portion of the groove 107.

Still referring to FIG. 3B, in some embodiments, the sleeve 104 is installed on the temperature-controlling cylinder 106 in the direction indicated by the arrow. In some embodiments, the sleeve 104 is sealed against the protruding portions of the groove 107, and the groove 107 then forms a pipe structure, i.e., the pipe 112.

Referring to FIG. 3C, in some embodiments, the annular cooling channel 301 is formed in the temperature-controlling cylinder 106 near the bottom opening 106B. In some embodiments, the annular cooling channel 301 has one end connected to the cooling fluid tank, and the flow directions of the cooling fluid are identified as R1, R2, and R3 sequentially.

In some embodiments, when the lower piston 108 is inserted in the testing chamber 110, the annular cooling channel 301 surrounds a portion of the lower piston 108. If the temperature of the lower piston 108 is too high, the annular cooling channel 301 can help cool the lower piston 108 by allowing the cooling fluid to flow around the portion of the lower piston 108.

Figure 4A:
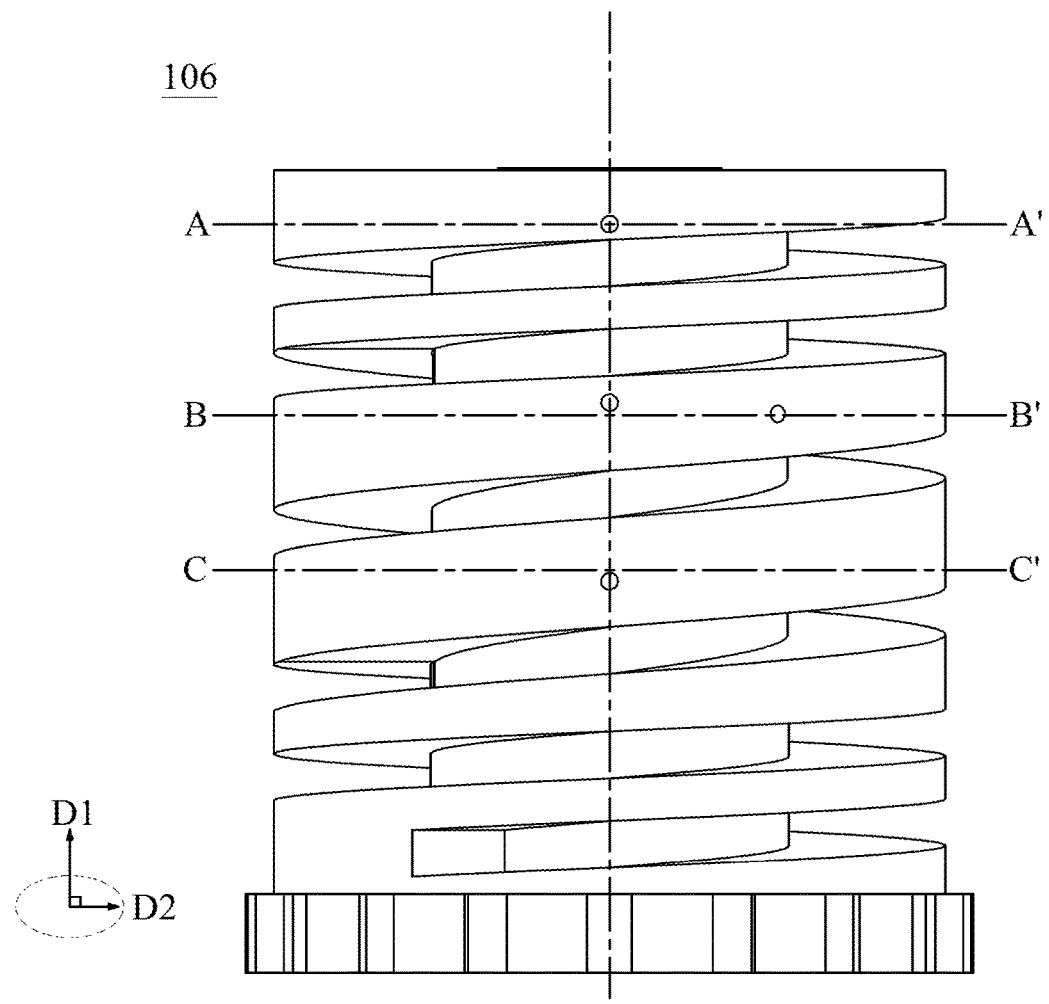
FIG. 4A is a side view of a temperature-controlling cylinder of the testing module in accordance with some embodiments of the present disclosure.
Figure 4B:
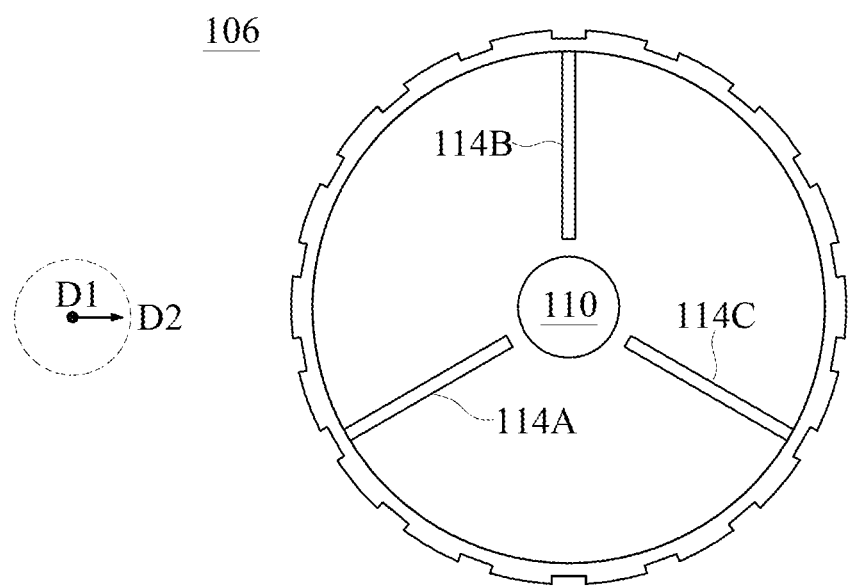
FIG. 4B illustrates a cross-sectional view of the temperature-controlling cylinder shown in FIG. 4A in accordance with some embodiments of the present disclosure.

FIG. 4A is a side view of the temperature-controlling cylinder 106 of the testing module 100 in accordance with some embodiments of the present disclosure; and FIG. 4B is a cross-sectional view of the temperature-controlling cylinder 106 of FIG. 4A.

Referring to FIGS. 4A and 4B, in some embodiments, the testing module 100 comprises temperature transducers 114A, 114B and 114C. In some embodiments, the temperature transducers 114A, 114B and 114C are inserted in the temperature-controlling cylinder 106 in approximately the radial direction D2. In some embodiments, the temperature transducers 114A, 114B and 114C have ends extending from several positions on an external surface of the temperature-controlling cylinder 106 and the other ends close to the testing chamber 110. In some embodiments, the several positions on the external surface do not overlap the pipes 112.

In some embodiments, the shortest distance between the temperature transducers 114A, 114B and 114C and the testing chamber 110 is about 0.5 mm. In some embodiments, the temperature transducers 114A, 114B and 114C are spaced by 120 degrees. In some embodiments, with the temperature transducers 114A, 114B and 114C, the temperature distribution of the specimen at different locations in the testing chamber 110 can be detected more precisely.

It should be noticed that although there are three temperature transducers shown in FIG. 4B for simplicity of explanation, any number of the temperature transducers may be used, as will be apparent to one of ordinary skill in the art upon consideration of the present disclosure. For example, four temperature transducers may be equally spaced (separated by 90 degrees) about the temperature-controlling cylinder 106.

In some embodiments, the temperature transducers are arranged at different surface levels. For example, the cross-sectional views along AA', BB', and CC' in FIG. 4A may all be represented by FIG. 4B. In addition, there are total nine temperature transducers used in the testing module 100. In some embodiments, there are temperature transducers arranged at more than three surface levels, and any number of the temperature transducers may be used in every surface level.

Figure 5A:
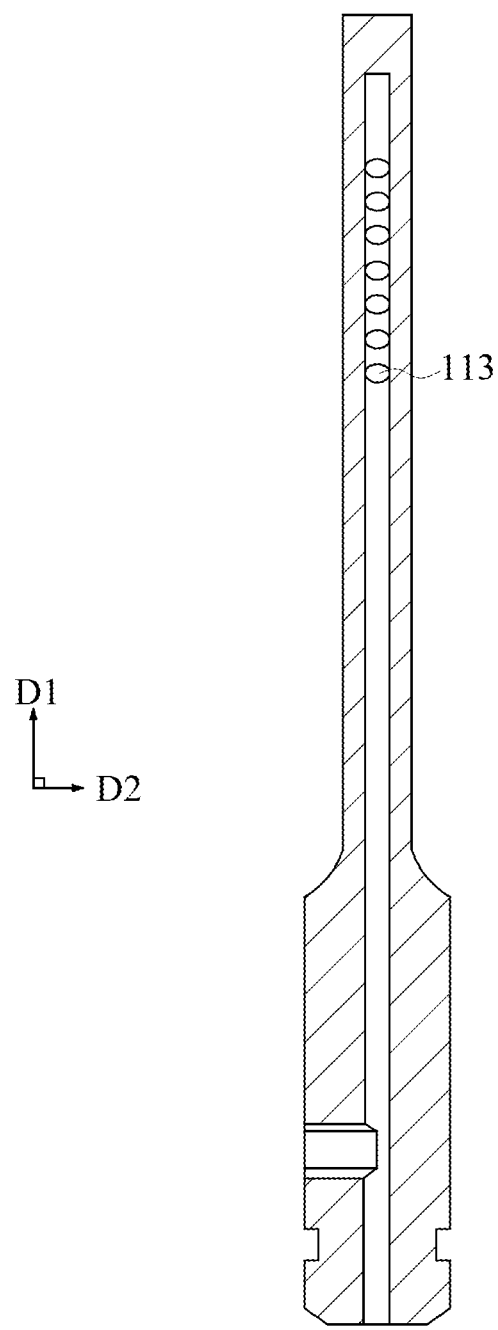
FIG. 5A is a cross-sectional view of a lower piston of the testing module in accordance with some embodiments of the present disclosure.

FIG. 5A is a cross-sectional view of the lower piston 108 of the testing module 100 in accordance with some embodiments of the present disclosure.

Referring to FIG. 5A, in some embodiments, the lower piston 108 has a wire 113 inside. The wire 113 has one end connected to a power supply. When the lower piston 108 is inserted in the temperature-controlling cylinder 106, the lower piston 108 can fine-tune the temperature in the testing chamber 110 with the wire 113. Therefore, the temperature distribution in the testing chamber 110 can be controlled more precisely. In addition, with the wire 113, the size of the lower piston 108 can be adjusted to compensate for thermal expansion and contraction. For example, when the lower piston 108 is rubbing or stuck in the testing chamber 110, the lower piston 108 can be cooled by reducing the voltage of the power supply. On the other hand, the voltage can be raised to allow the lower piston 108 to undergo a thermal expansion in order to prevent the specimen M from leaking into a gap between the lower piston 108 and the testing chamber 110.

Referring back to FIG. 1B, in some embodiments, the testing module 100 has three cooling pipes: the pipe 101C in the upper piston 102; the pipe 112 surrounding the testing chamber 110; and the annular cooling channel 301 surrounding the lower piston 108. It should be noted that the three cooling pipes can be controlled separately to allow flow of cooling liquids having different temperatures, velocities of flow, types of flow, etc.

In some embodiments, the testing module 100 has three wires: the wire 103C in the upper piston 102; the wire 109 surrounding the testing chamber 110; and the wire 113 inside the lower piston 108. It should be noted that the three wires can be controlled separately to provide different temperatures.

Under a measurement process, the lower piston 108 is configured to apply a pressure on the specimen M. In some embodiments, the lower piston 108 provides an isobaric environment, in which the pressure (P) is fixed, in the testing chamber 110. Under the isobaric environment, a relationship between the specific volume (V) and the temperature (T) of the specimen can be obtained by changing the temperature (T) in the testing chamber 110 through the wire 103C, wire 109 and wire 113.

In some embodiments, the wire 103C, wire 109 and wire 113 provide an isothermal environment, in which the temperature (T) is fixed, in the testing chamber 110. Under the isothermal environment, a relationship between the specific volume (V) and the pressure (P) of the specimen can be obtained by changing the pressure (P) with the lower piston 108.

Figure 5B:
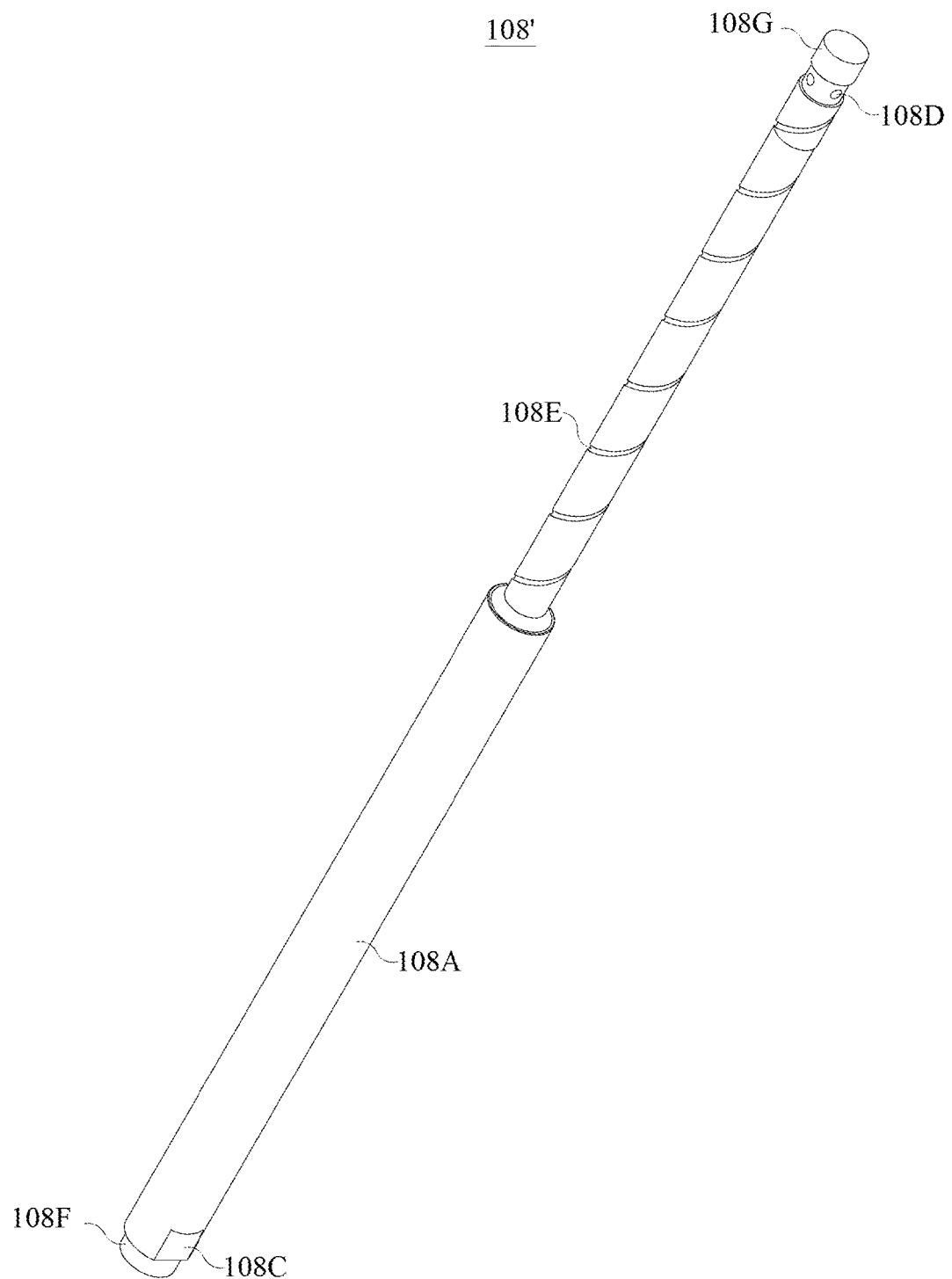
FIG. 5B is a full view and FIG. 5C is a cross-sectional view of a lower piston respectively in accordance with some embodiments of the present disclosure.
Figure 5C:
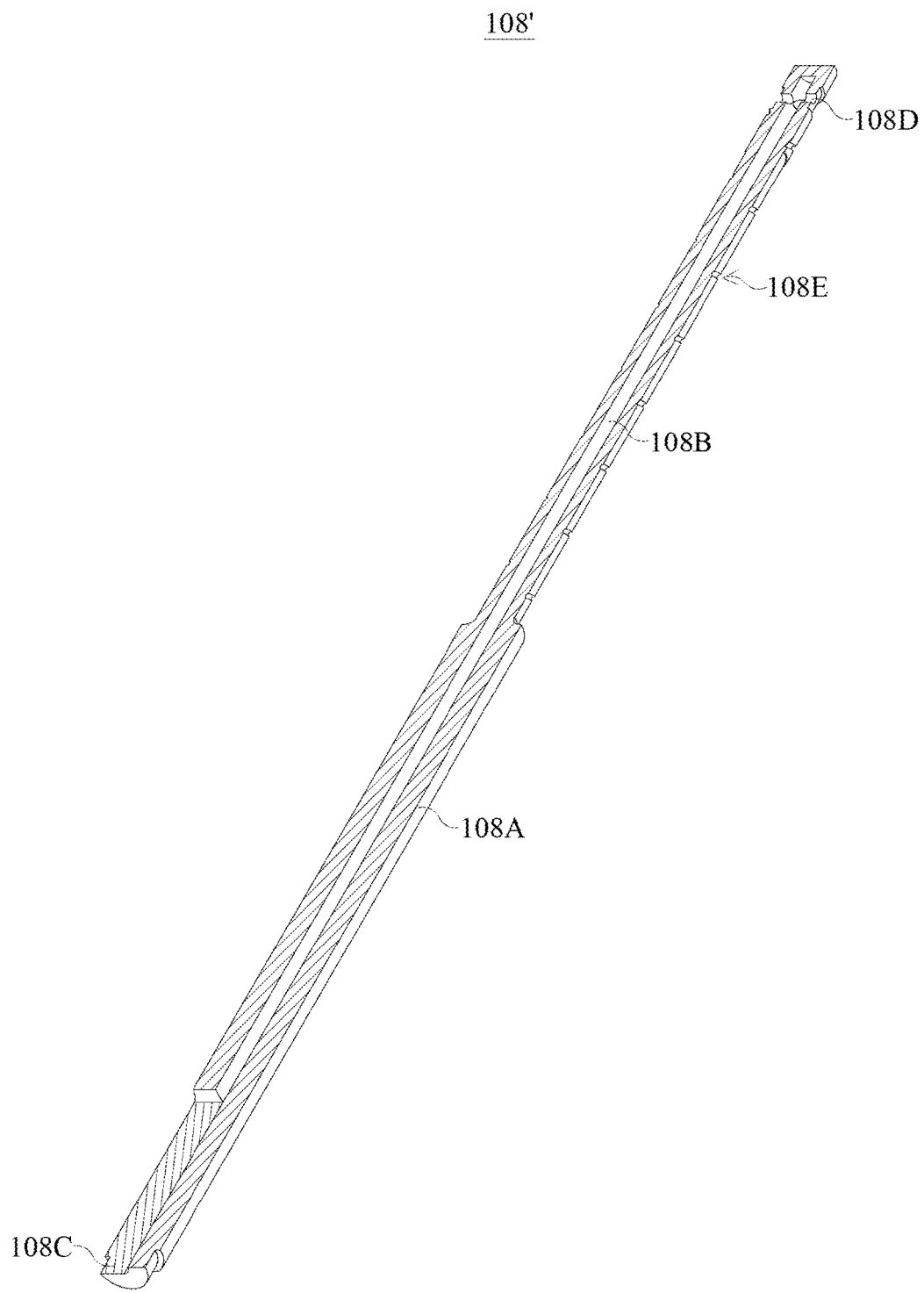

FIG. 5B is a full view and FIG. 5C is a cross-sectional view of a lower piston 108' respectively in accordance with some embodiments of the present disclosure. In some embodiments, the lower piston 108' comprises a body 108A having a hole 108B configured for receiving a heating device such as a heating wire, a fluid inlet 108C at a first end (tail end) 108F, a fluid outlet 108D at a second end (head end) 108G. In some embodiments, a cooling fluid such as the cooling air is transferred into the hole 108B through the fluid inlet 108C at the first end 108F, moves in the hole 108B from the first end 108F toward the second end 108G, and then is transferred out of the hole 108B through the fluid outlet 108D.

Referring to FIG. 5B and FIG. 1B, in some embodiments, the lower piston 108' has a groove 108E such as a spiral groove on the outer surface of the body 108A, and the spiral groove extends from the second end 108G toward the first end 108F. In some embodiments, during the testing, the cooling fluid from the fluid outlet 108D at the second end 108G is transferred toward the first end 108F through the groove 108E on the outer surface, rather than moving toward the specimen M in the chamber 110, so as to prevent the direct contact of the specimen M by the cooling fluid.

Figure 6:
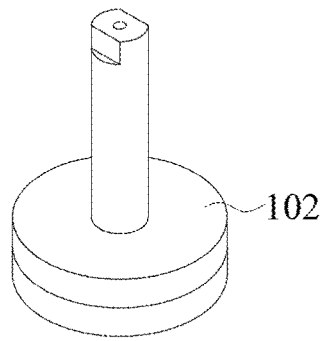
FIG. 6 is an exploded perspective view of a testing module in accordance with some embodiments of the present disclosure.
Figure 6:
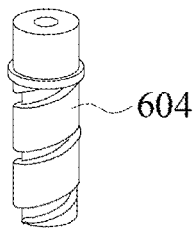
Figure 6:
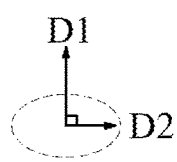
Figure 6:
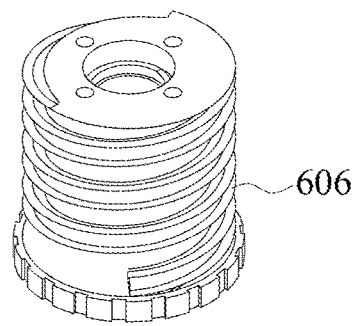
Figure 6:
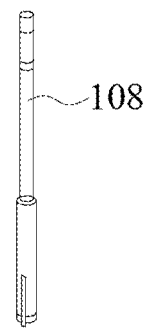

FIG. 6 is an exploded perspective view of a testing module 600 in accordance with some embodiments of the present disclosure. Since the testing module 600 is similar to that described above in relation to FIG. 1A, the identical numbers represent similar components for simplicity of explanation. Such similar components are omitted in the interest of brevity, and only the differences are provided.

Referring to FIG. 6, the testing module 600 comprises a testing tube 604, a temperature-controlling cylinder 606 receiving the testing tube 604, the upper piston 102 sealing an end of the testing tube 604, and the lower piston 108 sealing another end of the testing tube 604.

As with the testing module 100, the testing module 600 is installed in a measuring apparatus when used. A cooling fluid tank provides cooling fluid to cool the testing module 600. In some embodiments, the cooling fluid is vortex tube cooling gas for achieving rapid cooling.

Figure 7:
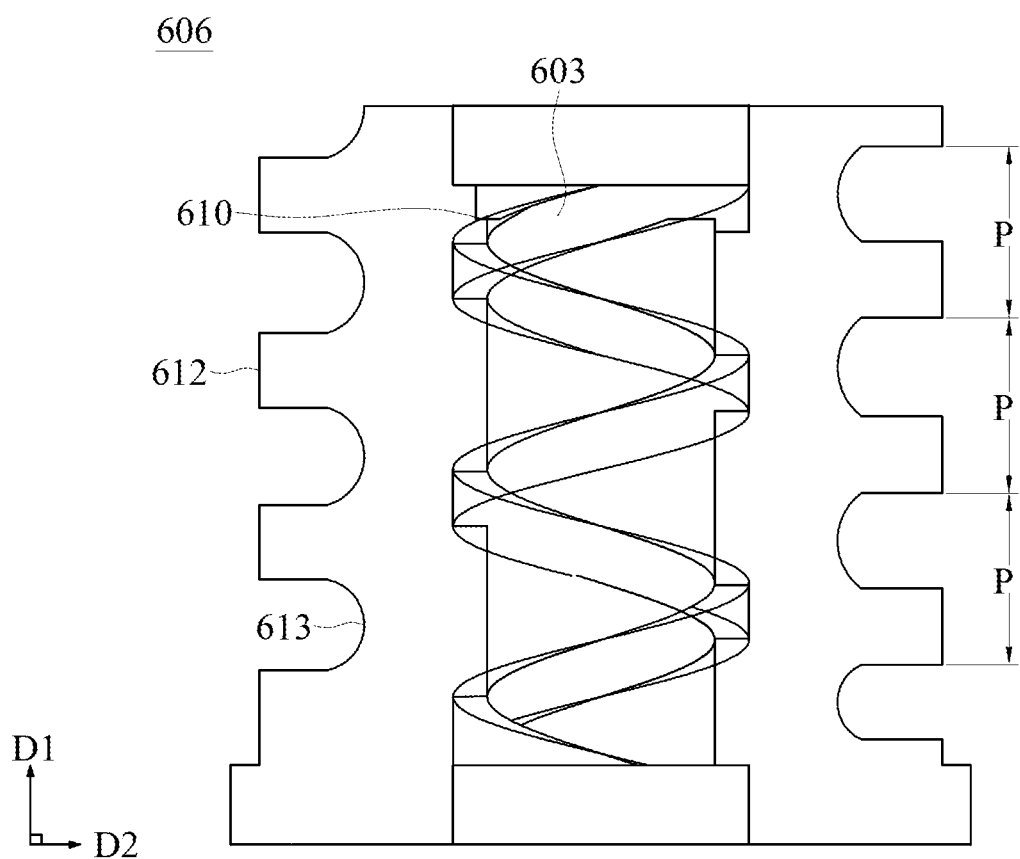
FIG. 7 is a perspective view of a temperature-controlling cylinder of the testing module in accordance with some embodiments of the present disclosure.

FIG. 7 is a perspective view of the temperature-controlling cylinder 606 of the testing module 600 in accordance with some embodiments of the present disclosure.

Referring to FIG. 7, the temperature-controlling cylinder 606 extends in the axial direction D1. The temperature-controlling cylinder 606 has a first internal surface 610 and a first external surface 612.

A wire (not shown in the figures) is provided on the first external surface 612 and surrounds the temperature-controlling cylinder 606 with a number of turns. As with the wire 109, in some embodiments, a density of the turns has at least two different values. In some embodiments, a density of the turns increases toward openings of the testing tube 604 when the testing tube 604 is received in the temperature-controlling cylinder 606.

Still referring to FIG. 7, in some embodiments, a groove 613 is recessed in the first external surface 612, approximately parallel to the radial direction D2. In some embodiments, the groove 613 surrounds the temperature-controlling cylinder 606 and winds in a spiral manner around the axial direction D1.

In some embodiments, the groove 613 has a varying pitch similar to that of the groove 107. In some embodiments, the groove 613 has a constant pitch P. The wire is wrapped in the groove 613 and surrounds the temperature-controlling cylinder 606, winding in a spiral manner along the axial direction D1.

Figure 8:
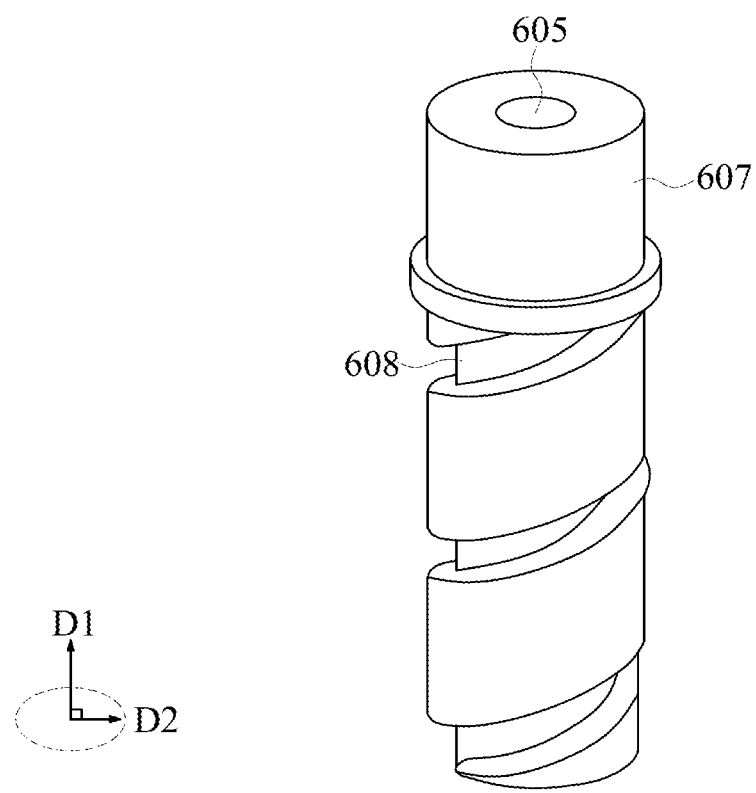
FIG. 8 is a perspective view of a testing chamber of the testing module in accordance with some embodiments of the present disclosure.

FIG. 8 is a perspective view of the testing tube 604 of the testing module 600 in accordance with some embodiments of the present disclosure.

Referring to FIG. 8, the testing tube 604 includes a second external surface 607. The testing tube 604 is received in the temperature-controlling cylinder 606 with the external surface 607 facing the first internal surface 610.

Still referring to FIG. 8, as with the temperature-controlling cylinder 106, the testing tube 604 has a top opening and a bottom opening. During a measurement process, the top opening is sealed by the surface 103B of the upper piston 102, and the bottom opening is sealed by the lower piston 108. Therefore, a testing chamber 605 is formed in the testing tube 604, wherein the testing chamber 605 has a longitudinal length L (not shown in the figures) in the axial direction D1. The longitudinal length L is measured from the top to the bottom of the testing chamber 605. More specifically, the longitudinal length L is the length of a space which is able to contain a specimen in the testing chamber 605.

The testing chamber 605 is similar to the testing chamber 110, and is configured to contain a specimen and keep the specimen under a specific environment, for example, an isobaric environment or an isothermal environment, during a measurement process.

In some embodiments, the testing chamber 605 is designed and shaped to receive the lower piston 108. A portion of the lower piston 108 is inserted into the testing tube 604. The specimen is placed on an end of the lower piston 108 in the testing chamber 605.

In some embodiments, relative sizes of the lower piston 108 and the testing chamber 605 are designed so that a pressure in the testing chamber 605 changes with movement of the lower piston 108 relative to the testing chamber 605 along the longitudinal length L.

In some embodiments, the heating devices of the testing module 600 include the wire 103C (shown in FIG. 2A) in the upper piston 102, a wire (not shown in the figures) surrounding the testing tube 604, and a wire 113 inside the lower piston 108.

In some embodiments, the flow passages of the cooling fluid in the testing module 600 include the pipe 101C (shown in FIG. 2A) in the upper piston 102 and a pipe between the temperature-controlling cylinder 606 and the testing tube 604. The pipe between the temperature-controlling cylinder 606 and the testing tube 604 can be implemented in two types: a recess in the testing tube 604, and a recess in the temperature-controlling cylinder 606.

With the type of the recess in the testing tube 604, a spiral groove 608 (shown in FIG. 8) is formed on the second external surface 607. When the testing tube 604 is received in the temperature-controlling cylinder 606, the first internal surface 610 of the temperature-controlling cylinder 606 is sealed against protruding portions of the spiral groove 608 and covers the spiral groove 608. Therefore, the spiral groove 608 is formed into a spiral pipe structure.

With the type of the recess in the temperature-controlling cylinder 606, a spiral groove 603 (shown in FIG. 7) is formed over the first internal surface 610. When the testing tube 604 is received in the temperature-controlling cylinder 606, the second external surface 607 of the testing tube 604 is sealed against protruding portions of the spiral groove 603 and covers the spiral groove 603. Therefore, the spiral groove 603 is formed into a spiral pipe structure.

As with the testing module 100, the testing module 600 comprises temperature transducers. The temperature transducers are inserted into the temperature-controlling cylinder 606 from the first external surface 612 approximately along the radial direction D2, and the temperature transducers have detecting ends close to the testing tube 604.

The temperature transducers have ends extending from several positions on the first external surface 612 and the other ends close to the testing chamber 604. The several positions on the first external surface 612 do not overlap the pipe between the temperature-controlling cylinder 606 and the testing tube 604.

FIG. 9A is a perspective view of a measuring apparatus 10 with the testing module in accordance with some embodiments of the present disclosure. FIG. 9B is a front view of the measuring apparatus 10 in FIG. 9A in accordance with some embodiments of the present disclosure.

Referring to FIGS. 9A and 9B, the upper piston 102 is attached to the measuring apparatus 10 at one end, and the other end would be sealed with the temperature-controlling cylinder 106 or the testing tube 604 in the temperature-controlling cylinder 606 during a measuring process.

The lower piston 108 is attached to the measuring apparatus 10 and configured to apply a force to the specimen in the temperature-controlling cylinder 106 or the testing tube 604 from the bottom.

The present disclosure provides a measuring apparatus for measuring a volumetric variation of a resin under different temperatures and pressures. In some embodiment, the measuring apparatus comprises a testing module. In some embodiments, the testing module comprises: a temperature-controlling cylinder having a top opening and a bottom opening; an upper piston and a lower piston respectively sealing the top opening and the bottom opening of the temperature-controlling cylinder so that a testing chamber is formed inside the temperature-controlling cylinder, wherein the testing chamber has a longitudinal length; and a pipe surrounding the testing chamber along the longitudinal length in such a way that when a wire is provided along and in the pipe with a number of turns, a density of the turns has at least two different values over the longitudinal length.

The present disclosure also provides a measuring apparatus for measuring a volumetric variation of a resin under different temperatures and pressures. In some embodiment, the measuring apparatus comprises a testing module. In some embodiments, the testing module comprises: a temperature-controlling cylinder having a first internal surface and a first external surface; a testing tube having a second external surface, received in the temperature-controlling cylinder with the second external surface facing the first internal surface; and an upper piston and a lower piston respectively sealing a top opening and a bottom opening of the testing tube so that a testing chamber is formed inside the testing tube, wherein the testing chamber has a longitudinal length; wherein a wire is provided on the first external surface, surrounding the testing chamber with a number of turns; and wherein a pipe is formed between the second external surface and the first internal surface, surrounding the testing chamber along the longitudinal length.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, and composition of matter, means, methods and steps described in the specification. As one of ordinary skill in the art will readily appreciate from the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A measuring apparatus, comprising:
a testing module, comprising:
a temperature-controlling cylinder having a top opening and a bottom opening; an upper piston and a lower piston respectively sealing the top opening and the bottom opening of the temperature-controlling cylinder to form a testing chamber inside the temperature-controlling cylinder, wherein the testing chamber has a longitudinal length; and
a pipe surrounding the testing chamber along the longitudinal length in such a way that when a wire is provided along and in the pipe with a number of turns, a density of the turns has at least two different values over the longitudinal length;
wherein the lower piston comprises a body having a hole configured for receiving a heating device, a fluid inlet at first end of the hole, a fluid outlet at second end of the hole, a groove on an outer surface of the body, and the groove extends from the second end to the first end.

2. The measuring apparatus of claim 1, wherein the pipe is constructed by a sleeve and an external wall of the temperature-controlling cylinder sealed against each other.

3. The measuring apparatus of claim 1, wherein the density of the turns increases toward the top opening and the bottom opening of the temperature-controlling cylinder.

4. The measuring apparatus of claim 1, wherein when a wire is provided along and in the pipe and a liquid flows in the pipe, the wire is isolated from the liquid by a component formed by means of brazing.

5. The measuring apparatus of claim 1, wherein the upper piston has a wire and a pipe that are positioned at different surface levels in such a way that the wire is closer than the pipe to the testing chamber.

6. The measuring apparatus of claim 1, wherein the upper piston has a connecting element attached to the measuring apparatus by means of a ball joint.

7. The measuring apparatus of claim 1, wherein a pressure in the testing chamber changes with a movement of the lower piston relative to the testing chamber along the longitudinal length.

8. The measuring apparatus of claim 1, further comprising an annular cooling channel in the temperature-controlling cylinder and near the bottom opening.

9. The measuring apparatus of claim 1, wherein an annular pipe is formed in the temperature-controlling cylinder and surrounds the lower piston.

10. The measuring apparatus of claim 1, wherein a plurality of temperature transducers are inserted into the temperature-controlling cylinder from several positions on the temperature-controlling cylinder that do not overlap the pipe and that are arranged to detect a temperature distribution in the testing chamber.

11. A measuring apparatus, comprising:
a testing module, comprising:
a temperature-controlling cylinder having a first internal surface and a first external surface;
a testing tube having a second external surface, received in the temperature-controlling cylinder with the second external surface facing the first internal surface; and
an upper piston and a lower piston respectively sealing a top opening and a bottom opening of the testing tube so that a testing chamber is formed inside the testing tube, wherein the testing chamber has a longitudinal length;
wherein a wire is provided on the first external surface, surrounding the testing chamber with a number of turns; and
wherein a pipe is formed between the second external surface and the first internal surface, surrounding the testing chamber along the longitudinal length;
wherein the lower piston comprises a body having a hole configured for receiving a heating device, a fluid inlet at first end of the hole, a fluid outlet at second end of the hole, and a groove on an outer surface of the body, wherein the groove extends from the second end to the first end.

12. The measuring apparatus of claim 11, wherein a groove is formed on the first external surface for providing the wire.

13. The measuring apparatus of claim 12, wherein a density of the turns increases toward the top opening and bottom opening of the testing tube.

14. The measuring apparatus of claim 11, wherein a spiral groove is formed on the second external surface and the pipe is constructed by the second external surface and the first internal surface sealing against each other.

15. The measuring apparatus of claim 11, wherein a spiral groove is formed on the first internal surface and the pipe is formed by the second external surface and the first internal surface sealing against each other.

16. The measuring apparatus of claim 11, wherein the upper piston has a wire and a cooling pipe that are positioned at different surface levels in such a way that the wire is closer than the cooling pipe to the testing chamber.

17. The measuring apparatus of claim 11, wherein the upper piston has a connecting element attached to the measuring apparatus by means of a ball joint.

18. The measuring apparatus of claim 11, wherein a pressure in the testing chamber changes with a movement of the lower piston relative to the testing chamber along the longitudinal length.

19. The measuring apparatus of claim 11, further comprising an annular cooling channel in the temperature-controlling cylinder and near the bottom opening.

20. The measuring apparatus of claim 11, wherein a plurality of temperature transducers are inserted into the testing tube from several positions not covered by the pipe, and the temperature transducers are arranged to detect a temperature distribution in the testing chamber.

\* \* \* \* \*